(12) United States Patent
Kaiser et al.

(10) Patent No.: US 8,293,174 B2
(45) Date of Patent: Oct. 23, 2012

(54) PRION DEACTIVATING COMPOSITION AND METHODS OF USING SAME

(75) Inventors: Nancy-Hope Elizabeth Kaiser, Pontoon Beach, IL (US); Jason F. Tirey, Ballwin, MO (US); Gerald E. McDonnell, Hants (GB)

(73) Assignee: American Sterilizer Company, Mentor, OH (US)

( * ) Notice: Subject to any disclaimer, the term of this patent is extended or adjusted under 35 U.S.C. 154(b) by 599 days.

(21) Appl. No.: 11/873,465

(22) Filed: Oct. 17, 2007

(65) Prior Publication Data

US 2009/0104073 A1   Apr. 23, 2009

(51) Int. Cl.
*A61L 2/00* (2006.01)
*G01N 33/00* (2006.01)
*G01N 31/12* (2006.01)

(52) U.S. Cl. .............................. 422/28; 422/94; 422/63

(58) Field of Classification Search ............... 422/94.63, 422/28, 94, 63
See application file for complete search history.

(56) References Cited

U.S. PATENT DOCUMENTS

| | | | |
|---|---|---|---|
| 5,374,555 A | 12/1994 | Pokora et al. | 435/278 |
| 5,633,349 A | 5/1997 | Rejchl | 530/364 |
| 6,387,858 B1 * | 5/2002 | Shah et al. | 510/161 |
| 6,437,102 B1 | 8/2002 | Lee et al. | 530/412 |
| 6,613,505 B2 | 9/2003 | Shih | 435/4 |
| 6,620,629 B1 | 9/2003 | Prusiner et al. | 436/543 |
| 6,719,988 B2 | 4/2004 | Prusiner et al. | 424/405 |
| 6,743,899 B2 | 6/2004 | Montalto et al. | 530/412 |
| 7,071,152 B2 | 7/2006 | McDonnell et al. | 510/161 |
| 2002/0172989 A1 | 11/2002 | Shih | 435/7.92 |
| 2002/0192731 A1 | 12/2002 | Shih | 435/7.92 |
| 2002/0197291 A1 * | 12/2002 | Ulbricht et al. | 424/401 |
| 2003/0073592 A1 | 4/2003 | McDonnell et al. | 510/161 |
| 2003/0086820 A1 | 5/2003 | McDonnell et al. | 422/28 |
| 2003/0148385 A1 | 8/2003 | Antloga et al. | 435/7.1 |
| 2004/0091474 A1 | 5/2004 | Raven et al. | 424/94.63 |
| 2004/0106188 A1 | 6/2004 | Kritzler et al. | 435/264 |
| 2005/0026269 A1 * | 2/2005 | Kottwitz et al. | 435/222 |
| 2005/0032913 A1 | 2/2005 | McDonnell et al. | 514/731 |
| 2006/0030505 A1 | 2/2006 | Biering et al. | 510/375 |
| 2006/0105930 A1 * | 5/2006 | McDonnell et al. | 510/161 |
| 2006/0127390 A1 * | 6/2006 | Hoglund et al. | 424/94.64 |
| 2006/0134092 A1 | 6/2006 | Miwa et al. | 424/94.63 |
| 2006/0228696 A1 | 10/2006 | Rohwer et al. | 435/5 |

(Continued)

FOREIGN PATENT DOCUMENTS

EP   0 358 500 A1   3/1990

(Continued)

OTHER PUBLICATIONS

Dickinson et al.; "Prionzyme; a new enzymatic approach to the decontamination of surgical instruments and contaminated animal waste product"; Health Protection Agency, Neuro Prion, 2006, 1 page.

(Continued)

*Primary Examiner* — Kevin Joyner
(74) *Attorney, Agent, or Firm* — Renner, Otto, Boisselle & Sklar, LLP

(57) ABSTRACT

The disclosed invention relates to prion deactivating compositions and methods for using the same. The prion deactivating composition may comprise at least one prion denaturing agent and at least one prion deactivating enzyme. The invention relates to a method of cleaning and/or sterilizing a material contaminated with infectious proteins.

18 Claims, 10 Drawing Sheets

Example 2A

Example 2B

Example 3

Example 4

U.S. PATENT DOCUMENTS

| | | | |
|---|---|---|---|
| 2006/0270571 A1* | 11/2006 | Burke et al. | 510/130 |
| 2007/0037723 A1 | 2/2007 | McDonnell et al. | |
| 2008/0248556 A1* | 10/2008 | Koenig et al. | 435/262.5 |

FOREIGN PATENT DOCUMENTS

| | | |
|---|---|---|
| WO | 99/42829 | 8/1999 |
| WO | 99/51279 | 10/1999 |
| WO | 02/053723 A2 | 7/2002 |
| WO | 02/092014 A2 | 11/2002 |
| WO | 03/090875 | 11/2003 |
| WO | 2005/083443 A2 | 9/2005 |
| WO | 2006/015189 | 2/2006 |
| WO | 2008/057293 | 5/2008 |

OTHER PUBLICATIONS

Jackson et al.; "An enzyme-detergent method for effective prion decontamination of surgical steel"; *Journal of General Virology* (2005), 86, pp. 869-878.

Langeveld et al.; "Enzymatic Degradation of Prion Protein in Brain Stem from Infected Cattle and Sheep"; *JID* 2003:188, Electronically Published Nov. 18, 2003; pp. 1782-1789.

Yoshioka et al.; "Characterization of a proteolytic enzyme derived from a *Bacillus* strain thta effectively degrades prion protein"; *Journal of Applied Microbiology* 102 (2007); pp. 509-515.

International Search Report and Written Opinion, Application No. PCT/US2008/080255, mailed Oct. 8, 2009.

Fichet et al.; "Novel methods for disinfection of prion-contaminated medical devices"; *The Lancet*; vol. 364, Aug. 7, 2004; pp. 521-526.

Sgiurdsson et al.; "Copper Chelation Delays the Onset of Prion Disease"; *The Journal of Biological Chemistry*; Vo. 278, No. 47, Nov. 21, 2003; pp. 46199-46202.

Jerome Solassol et al.; The Journal of Infectious Diseases; 2006:194 (Sep. 15); A Novel Copper-Hydrogen Peroxide Formulation for Prion Decontamination; pp. 865-869.

Simmer; "Prions: Infectious Proteins Responsible for Mad Cow Disease"; *The Science Creative Quarterly*; Issue Two, Aug. 2003.

* cited by examiner

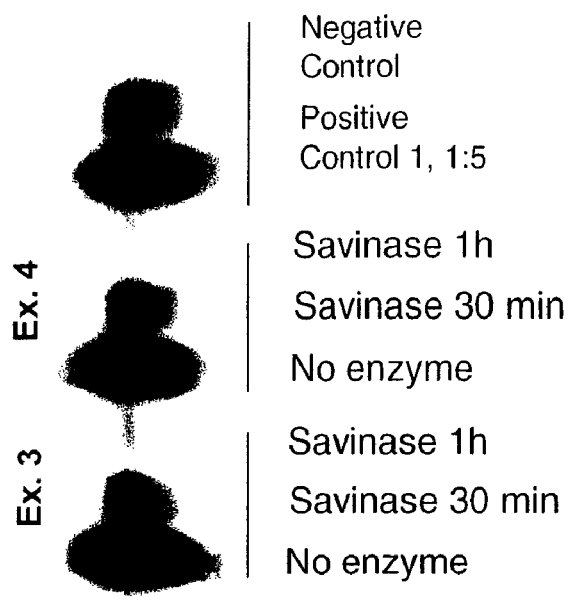
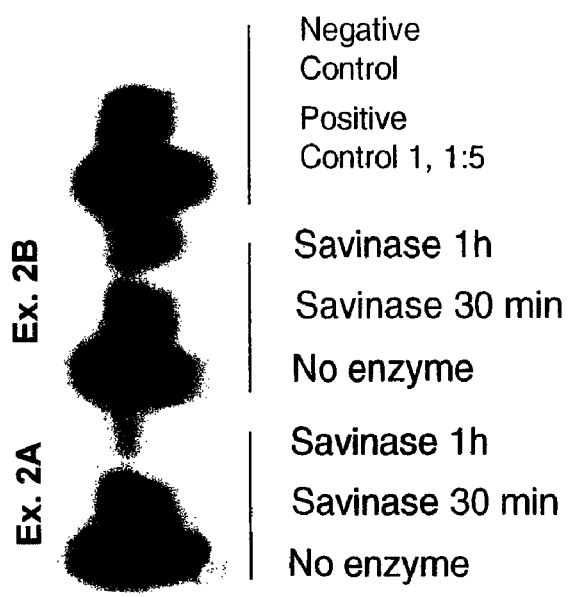
FIG. 5

PRION DEACTIVATING COMPOSITION AND METHODS OF USING SAME

TECHNICAL FIELD

This invention relates to prion deactivating compositions and to methods for using the same.

BACKGROUND

The term "prion" is used to describe proteinaceous-infectious agents that cause relatively similar brain diseases in humans and/or in animals, which are invariably fatal. These diseases are generally referred to as transmissible spongiform encephalopathies (TSEs). TSEs include Creutzfeldt-Jakob disease (CJD) and variant CJD (vCJD) in humans, bovine spongiform encephalopathy (BSE) in cattle (also known as "mad cow disease"), scrapie in sheep, and wasting disease in elk. All of these diseases attack the neurological organs of humans and/or animals which are susceptible to the diseases. They are characterized by initially long incubation times followed by a short period of neurological symptoms, including dementia and loss of coordination, and eventually death.

The infectious agent responsible for these diseases is believed to be a simple protein with no associated nucleic acids. The pathogenic mechanism for such prion diseases is proposed to involve an initially normal host encoded protein. A prion is actually a normal host encoded protein (PrP) that exists in a first conformational state in a non-infected host. The protein undergoes a conformational change to a second, abnormal conformational state, which has the ability of self-propagation. For example, a normal host encoded protein may exist in a first conformational state $PrP^c$ (cellular) in a non-infected host and then change to a second conformational state, such as $PrP^{Sc}$ (in the disease scrapie), in infected hosts. Despite being chemically similar to each other, the abnormal prion form differs from the normal host encoded protein with respect to higher-order structure (i.e., secondary, tertiary, and/or quaternary structure) and solubility. With scrapie, for example, one difference between the scrapie form ($PrP^{Sc}$) and the cellular form is in the secondary structure of $\alpha$-helixes as compared to $\beta$-pleated sheets. $PrP^{Sc}$ has a higher $\beta$-pleated sheet content compared to the normal cellular prion protein structure.

The exact cause or reason for the change from the normal conformational state to the abnormal (infected) conformational state is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Prion diseases may thus be classified as a protein aggregation disease, which also includes several other fatal diseases, such as Alzheimer's disease and amyloidosis. In the case of CJD, the most prevalent prion disease in humans, about 85% of cases are thought to arise sporadically, about 10% are thought to be inherited, and about 5% arise iatrogenically. Associated diseases may also include haemozoin precipitation during malarial parasite infection.

Although not considered to be highly contagious, prion diseases can be transmitted by certain high-risk tissues, including the brain, spinal cord, cerebral spinal fluids, and the eye. Iatrogenic transmission has been reported during several procedures, including dura-mater grafting, corneal transplants, pericardial homografts, and through human gonadotropin and human growth hormone contamination. Problems with blood transmission have been reported.

SUMMARY

A problem with prion diseases is that they can be transmitted via medical devices, including neurosurgical instruments, depth electrodes, and other devices used for surgical procedures in close proximity to the central nervous system. Procedures previously considered to be "low risk" in terms of prion infection, such as tonsillectomy and dental procedures, may pose unacceptable risks of infection, particularly, if the incidence of prion-related diseases increases.

After a surgical procedure on a prion infected patient (which may be known or, as in most cases, unknown), prion containing residue may remain on the surgical instruments, particularly neurosurgical and opthalmological instruments. During the long incubation period, it is extremely difficult to determine whether a surgical candidate is a prion carrier.

Different levels of microbial decontamination may include sanitization, disinfection and sterilization. Sanitation connotes free from dirt or germs by cleaning. Disinfection calls for cleansing in order to destroy harmful microorganisms. Sterilization, the highest level of biological contamination control, connotes the destruction of all living microorganisms.

Various biological materials, which do not live or reproduce in the conventional sense, such as prions, are, nevertheless, capable of multiplication and/or transformation into harmful entities. As used herein, the term "deactivation" encompasses the destruction of such harmful biological materials, such as prions, and/or their ability to replicate or undergo conformational changes to harmful species.

Prions are notoriously very hardy and demonstrate unique resistance to routine methods of decontamination (including cleaning, disinfection and sterilization). Unlike microorganisms, prions have no known DNA or RNA to destroy or disrupt. Prions, due to their hydrophobic nature, tend to aggregate together in insoluble clumps. Under many conditions that lead to successful sterilization of microorganisms, prions form tighter clumps, which can protect them and underlying prions from the sterilization process.

The World Health Organization (1999) recommendations for prion deactivation calls for soaking surgical instruments in concentrated sodium hydroxide or hypochlorite for two hours followed by one hour in an autoclave. These aggressive treatments are often incompatible with medical devices, particularly flexible endoscopes and other devices with plastic, brass, or aluminum parts. Many devices are damaged by exposure to high temperatures. Further, these procedures are only recommended when cases of prion disease are known or highly suspected. Chemical treatments employing highly alkaline solutions, such as those with a pH of greater than about 12, are damaging to medical device materials or surfaces in general. Glutaraldehyde, formaldehyde, ethylene oxide, simple liquid hydrogen peroxide, most phenolics, alcohols, and processes such as dry heat, boiling, freezing, UV, ionizing, and microwave radiation have generally been reported to be ineffective under the test conditions described.

There is a need for products and methods for treating materials contaminated with infectious proteins, including materials infected with prions. Further, there is a need for products and methods that are effective against prions yet compatible with the materials (e.g., surfaces or articles) being treated. Thus, in one aspect, there is a need for products and methods that are effective against prions at a relatively low pH, that is, at a pH of up to about 12. The present invention fulfills these needs by providing for the treatment of infected material using the inventive prion deactivating composition.

The inventive prion deactivating composition may comprise at least one prion denaturing agent and at least one protein deactivating enzyme. The composition may further comprise one or more membrane disrupting agents, surfactants, cosolvents, coupling agents, corrosion inhibitors, activity enhancing agents, enzyme stabilizers, oxidizing agents, reducing agents, acids, defoamers, or a mixture of two or more thereof. The foregoing ingredients may be dispersed or dissolved in a suitable solvent such as water.

The invention may relate to a method of cleaning a material that is contaminated with infectious proteins, the method comprising contacting the material with a prion deactivating composition, the prion deactivating composition comprising at least one prion denaturing agent and at least one prion deactivating enzyme. The contacting with the prion denaturing agent and the prion deactivating enzyme may occur simultaneously or sequentially. When contacting sequentially, either the prion denaturing agent or the prion deactivating enzyme may initially contact the contaminated material. Separate compositions or solutions containing these may be used.

The invention may relate to a method of sterilizing a material that is contaminated with infectious proteins, the method comprising: (a) contacting the material with a prion deactivating composition, the prion deactivating composition comprising at least one prion denaturing agent and at least one prion deactivating enzyme; and (b) exposing the material to a sterilization medium. The contacting with the prion denaturing agent and the prion deactivating enzyme may occur simultaneously or sequentially. When contacting sequentially, either the prion denaturing agent or the prion deactivating enzyme may initially contact the contaminated material. Separate compositions or solutions containing these may be used.

BRIEF DESCRIPTION OF THE DRAWINGS

FIGS. 1-5 show western blot test results for the tests reported in Example 5.

DETAILED DESCRIPTION

Figure 1:
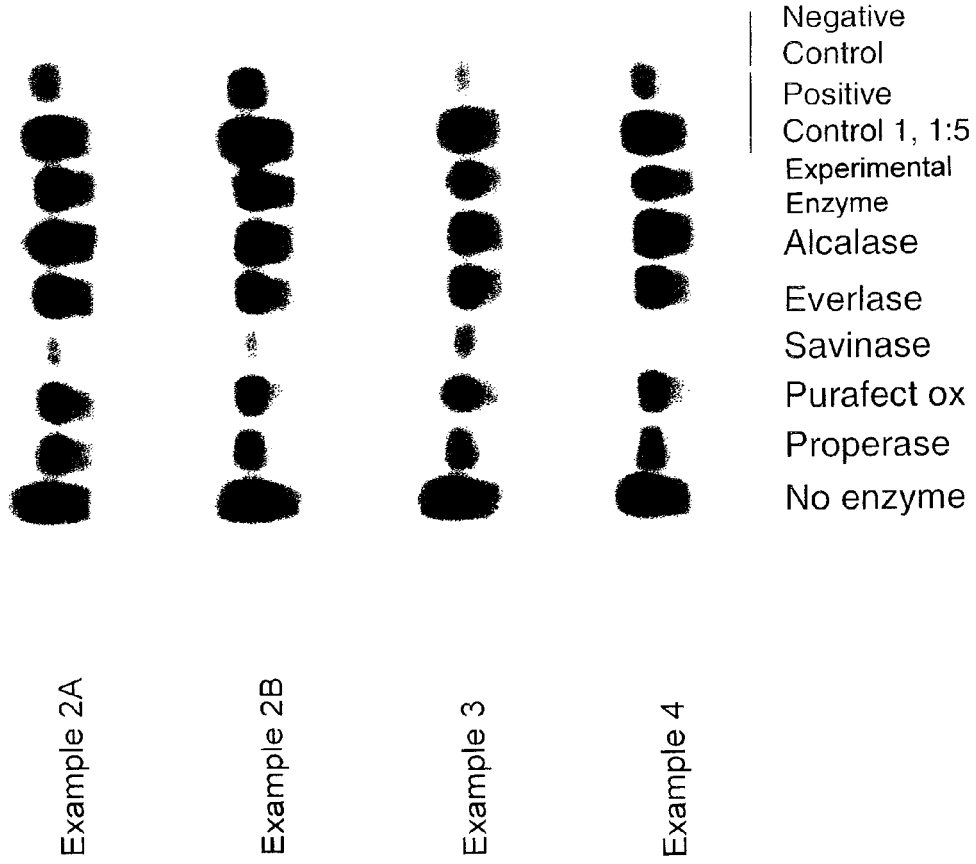
Figure 2:
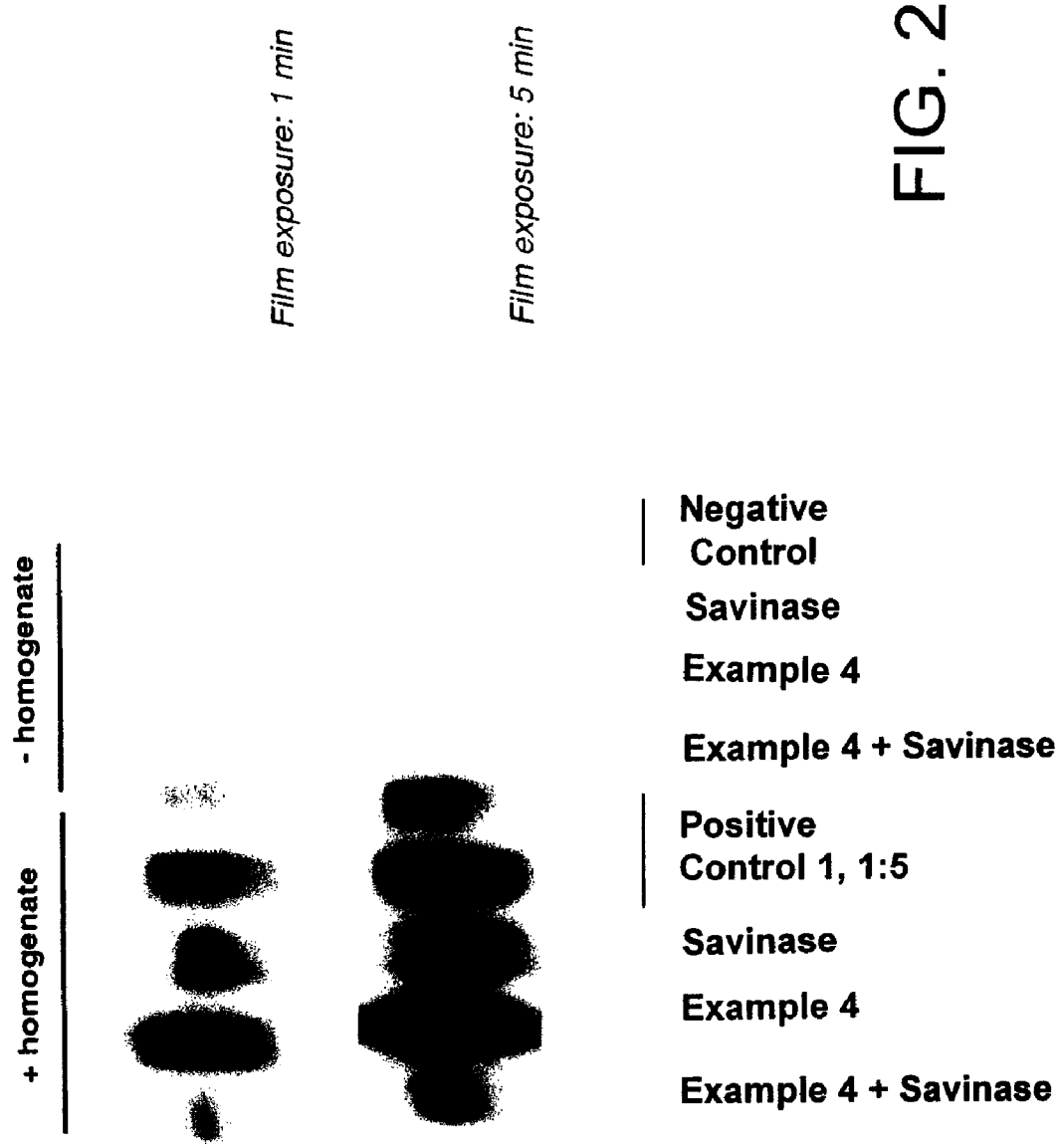
Figure 3:
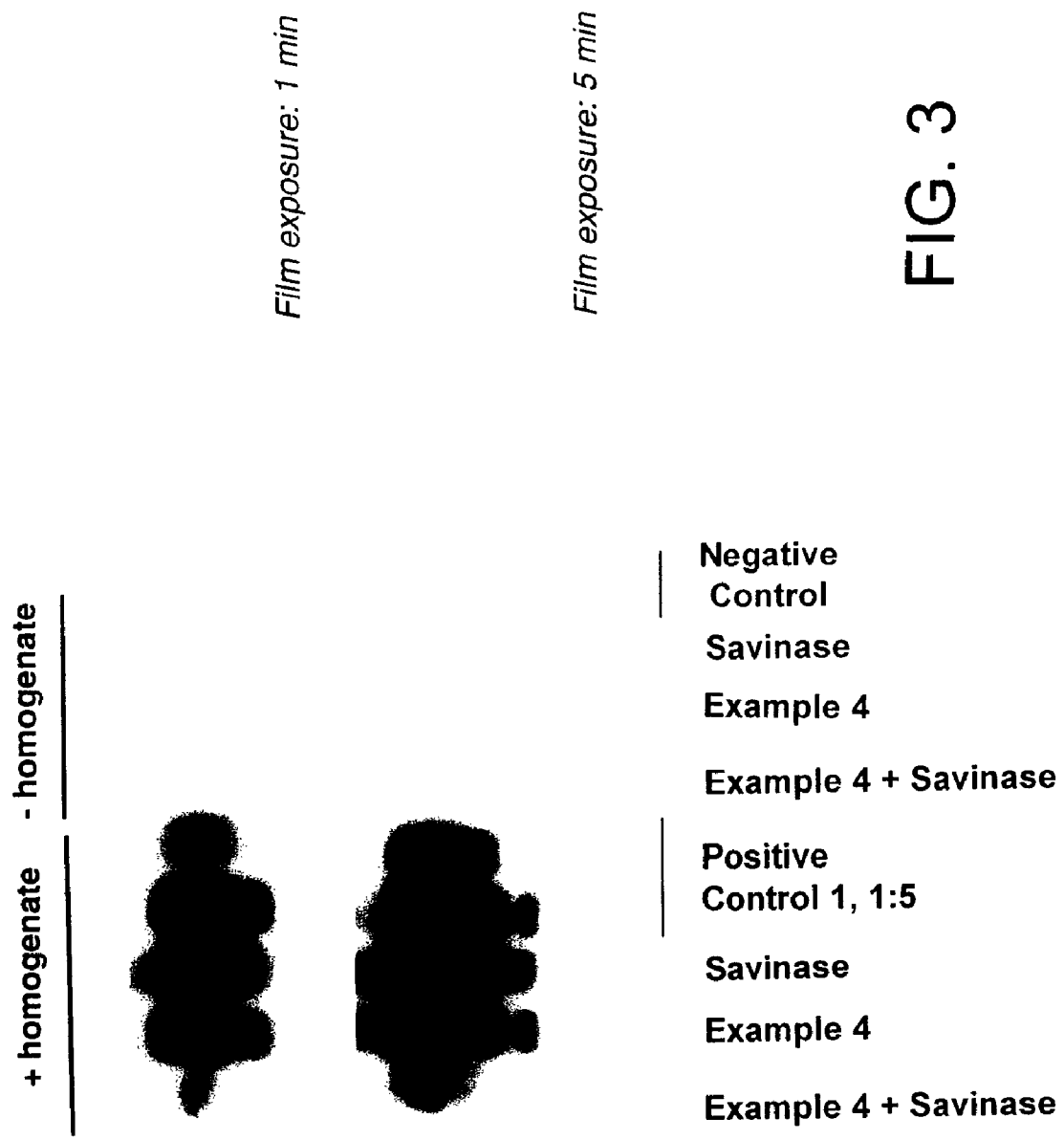
Figure 4:
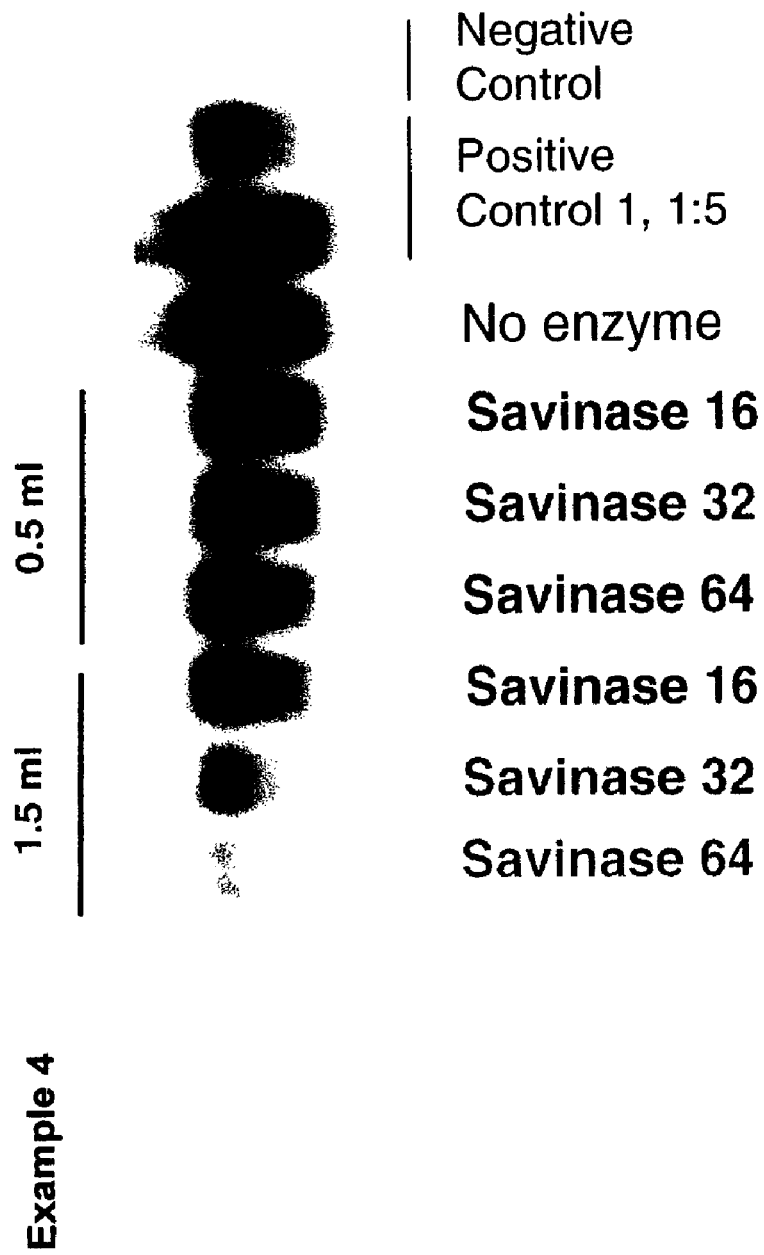

All ranges and ratio limits disclosed in the specification and claims may be combined. It is to be understood that unless specifically so specified, references to "a," "an" and/or "the" may include one or more than one, and that reference to an item in the singular may also include the item in the plural.

The term "prion deactivating composition" refers to a composition which is suitable for destroying prions and/or reducing the ability of prions to replicate or undergo conformational changes to harmful species.

The term "denature," or variances thereof, encompasses any change in a protein's higher order structure including, for example, any change to a protein's secondary, tertiary, and/or quaternary structure. Generally, the term "denature" encompasses any non-covalent change to a protein's structure. That is, "denature" encompasses any change to a protein's structure except cleavage of peptide bonds in a protein's primary structure. The term "denature" does, however, encompass covalent changes that may be associated with higher order protein structures, such as, for example, internal cross-linking, e.g., internal cross-linking formed by disulfide bonds, and the like. The degree of denaturation is not particularly limited and does not necessarily have to be a complete structural change from any of a quaternary structure to a tertiary structure, a tertiary structure to a secondary structure, a first secondary structure to a second secondary structure, etc.

The term "prion denaturant" or "prion denaturing agent" includes any material that is capable of denaturing a prion, e.g., causing a prion to undergo a change in structural conformation including, for example, causing changes to a prion's secondary, tertiary, or quaternary structures. The terms "prion denaturant" and/or "prion denaturing agent" encompass materials that interact with (1) a prion that exists in the abnormal or infected conformational state so as to cause the prion to undergo a change in structural conformation, and/or (2) a prion that exists in a normal (uninfected) conformational state (e.g., in the normal host encoded protein state) so as to cause the prion to undergo a change in structural conformation. The degree to which a prion undergoes a structural change in the presence of a "prion denaturant" is not limited to complete changes to a structural conformation. For example, a prion denaturant need not cause a prion to undergo a complete structural change such as from any of a quaternary structure to a tertiary structure, a tertiary structure to a secondary structure, a first secondary structure to a second secondary structure, a secondary structure to an unfolded, primary structure, etc. Rather, changes in a prion's structural conformation include any change or disruption to a prion's structural conformation. For example, a prion denaturing agent may cause a prion to undergo a conformational change to a sufficient degree such that the prion exhibits some susceptibility to deactivation such as, for example, enzymatic cleavage by a proteolytic enzyme. Additionally, as used herein, a "prion denaturant" or "prion denaturing agent" encompasses a material that is capable of preventing a prion in the normal host encoded protein form or conformation from assuming a structural conformation (including secondary, tertiary, or quaternary structures) associated with an abnormal (infected) state and in which the protein would be relatively resistant to enzymatic cleavage or deactivation.

The term "prion deactivating enzyme" refers to any enzyme that is capable of deactivating a prion. In one embodiment, a prion deactivating enzyme includes enzymes capable of deactivating a prion through at least one of peptide bond change, disulfide bond change, cross-linking, or combinations of two or more thereof.

The term "complexing agent" refers to a compound that contains one or more groups capable of bonding to a central atom by at least one coordinating atom. The complexing agent may include unidentate ligands as well as multidentate ligands. The complexing agent may be a chelating agent.

The term "sterilization" refers to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term "sterilization" may be used herein to also refer to processes less rigorous than sterilization, for example, disinfection, sanitization, decontamination, cleaning, and the like. Similarly, variations of term "sterilization," such as steriliant, sterilizing, etc., may also be used herein to refer to and encompass related variants associated with processes less rigorous than sterilization (e.g., disinfectant, disinfecting, etc.)

The present invention relates to prion deactivating compositions and methods of using such compositions to treat or clean surfaces contaminated with infectious proteins. The infectious proteins may include prions. The prion deactivating composition may comprise at least one prion denaturing agent and at least one prion deactivating enzyme. The weight ratio of the at least one prion denaturing agent to the at least one prion deactivating enzyme may be in the range from about 1:50 to about 50:1, and in one embodiment in the range from about 1:25 to about 25:1, and in one embodiment in the range from about 1:15 to about 15:1, and in one embodiment in the range from about 1:10 to about 10:1, and in one embodiment in the range from about 1:7 to about 7:1, and in one embodiment in the range from about 1:5 to about 5:1. The prion deactivating composition may further comprise one or more membrane disrupting agents, activity enhancing agents, cosolvents, surfactants, coupling agents, corrosion inhibitors, enzyme stabilizers, oxidizing agents, reducing agents, acids, defoamers, or a mixture of two or more thereof. The foregoing components may be dispersed or dissolved in water.

The prion denaturing agent may comprise any material suitable for denaturing a prion. Denaturation may include any change to a prion's protein structure including changes to a prion's quaternary, tertiary, and/or secondary structures. The prion denaturing agent may also denature a prion by disrupting internal or external cross-linking associated with a prion. The prion denaturing agent may comprise one or more copper (II) complexing agents, disulfide bond cleaving agents, or a mixture of two or more thereof, and the like. The copper (II) complexing agents may include copper (II) chelating agents. The prion denaturing agent may be present in the inventive prion deactivating composition at a concentration in the range from about 0.0001 to about 60 percent by weight, and in one embodiment in the range from about 0.01 to about 50 percent by weight, and in one embodiment in the range from about 0.01 to about 40 percent by weight, and in one embodiment in the range from about 0.1 to about 20 percent by weight, and in one embodiment in the range from about 0.1 to about 15 percent by weight, and in one embodiment in the range from bout 0.1 to about 10 percent by weight, and in one embodiment from about 0.2 to about 5 percent by weight, and in one embodiment from about 0.3 to about 3 percent by weight.

The copper (II) complexing agent may comprise any material capable of complexing copper (II) ions, salts of copper (II) ions, or mixtures of two of more thereof. The copper (II) complexing agent may be capable of complexing (i) free copper (II) ions and/or salts thereof from an environment infected with prion material, and/or (ii) copper (II) ions and/or salts thereof associated with a prion material such as, for example, copper (II) ions and/or salts thereof bound to or complexed with a prion. The copper (II) complexing agents may include ethylenediaminetetraacetic acid (EDTA); salts of EDTA; 1,1-hydroxyethylidene-1,1 diphosphonic acid (HEDP); salts of HEDP; aminotris(methylene phosphonic acid) (ATMP); salts of ATMP; diethylenetriaminepentamethylenephosphonic acid (DTPMPA); salts of DTPMPA; ethylenediaminedisuccinic acid (EDDS); etidronic acid; salts of etidronic acid; azoles; mixtures of two or more thereof, and the like. The salts of EDTA may include tetrasodium EDTA. The salts of etidronic acid may include tetrasodium etidronate (available as Turpinal 4NL from Dequest) and disodium etidronate (available as Turpinal SL from Dequest). The azoles may include the triazoles, such as benzotriazole, tolyltriazole, carboxybenzotriazole, mixtures of two or more thereof, and the like. Salts of the triazoles such as sodium tolyltriazole may be used. Salts of didecyldimethylammonium with tolyltriazole, benzotriazole, carboxybenzotriazole, ethanol-2,2'-[[methyl-1H-benzotriazol-1-yl)methyl]imino]bis-, mixtures of two or more thereof, and the like, may be used. The complexing agents may include tetrasodiumethylenediaminedisuccinic acid (Octaquest A65 from Innospec); trisodiummethylglycinediacetic acid (Trilon M from BASF); tetrasodiumtriiminodisuccinic acid (Baypure CX100 from Chesham); L-glutamic acid N,N-diacetic acid tetrasodium salt (Dissolvine GL from Akzo Nobel); 6,6'6''-(1,3,5-triazine-2,4,6-triyltriimino) tris(hexanoic acid) (Irgacor L190 from Ciba); ethanol-2,2'-[[methyl-1H-benzotriazol-1-yl)methyl]imino]bis- (Irgamet 42 from Ciba); didecyldimethylammonium bicarbonate/carbonate (CarboShield 1000 from Lonza Incorporated).

The copper (II) complexing agent may be present in the inventive prion deactivating composition in an amount suitable for binding an effective amount of copper (II) ions, salts thereof, or mixtures of two or more thereof such that a prion denatures (e.g., undergoes a conformational change from an abnormal state or is prevented from assuming an abnormal conformation). The copper (II) complexing agent may be present in the prion deactivating composition at a concentration in the range up to about 50 percent by weight, and in one embodiment in the range from about 0.0001 to about 50 percent by weight, and in one embodiment from about 0.01 to about 25 percent by weight, and in one embodiment from about 0.1 to about 10 percent by weight, and in one embodiment from about 0.2 to about 7 percent by weight, and in one embodiment from about 0.3 to about 5 percent by weight.

Without being bound by theory, it is believed that prions may be copper binding proteins and involved in cellular transportation of copper ions. Copper may stimulate endocytosis of cellular non-infected prions from the cell surface. Additionally, there may be a relatively high copper content associated with the prion protein brain homogenates present in the form of copper (II). The copper (II) complexing agents that may be employed in the inventive compositions may bind or complex the copper (II) ions and cause the prion to denature. Denaturing resulting from the complexing of copper (II) ions and/or salts thereof may include changes to a prion's structural conformation when the prion is in an abnormal (infectious) conformation, and/or a normal, host encoded protein conformation. Denaturing resulting from the complexing of copper (II) ions and/or salts thereof may also include situations in which a prion in the normal host encoded protein conformation is prevented from complexing copper (II) ions and thereby assuming an abnormal (infectious) conformation.

The disulfide bond cleaving agents may comprise one or more of thioglycolate, urea, sodium thiocyanate, glutathione, guanidinium hydrochloric acid, iodoacetic acid, and the like, or a mixture of two or more thereof. The disulfide bond cleaving agent may be present in the inventive prion deactivating composition at a concentration in the range up to about 60% by weight, and in one embodiment in the range from about 0.01 to about 60 percent by weight, and in one embodiment in the range from about 0.1 to about 40 percent by weight, and in one embodiment in the range from about 5 to about 40 percent by weight, and in one embodiment in the range from about 5 to about 35 percent by weight, and in one embodiment in the range from about 10 to about 30 percent by weight.

The prion deactivating enzyme may comprise one or more proteolytic enzymes (also referred to as proteases or peptidases) that are capable of deactivating prions. The prions may be deactivated by the cleaving of peptide bonds. The prion deactivating enzyme may comprise a specific protease, a non-specific protease, or a mixture of two or more thereof. The protease may be natural or synthetic. The protease may include bromelain, pepsin and/or papain. The protease may include subtilisins, thermolysins, bacterial protease, proteases exhibiting collagenase activity, proteases which hydrolyze gelatin, and the like. The protease may be a serine protease. The prion deactivating enzyme may comprise at least one non-specific serine protease produced by a genetically modified *Bacillus*, at least one non-specific protease produced by *Bacillus lichenformis*, or a mixture thereof. The protease enzymes may include those available from Novozymes under the tradenames Alcalase®, Esperase®, Savinase® and Ovozyme®. Also included are the protease enzymes available from Genencor under the tradenames Purafect®L, Purafect®MA L, Properase L and Multifect®. The protease available from Enzyme Solutions Pty Ltd. under the name GC 106 may be used. Mixtures of two or more of the foregoing may be used. The prion deactivating enzyme may be present in the prion deactivating composition at a concentration in the range from about 0.001 to about 70 percent by weight, and in one embodiment in the range from about 0.5 to about 50 percent by weight, and in one embodiment from about 0.5 to about 40 percent by weight, and in one embodiment from about 0.5 to about 35 percent by weight, and in one embodiment from about 0.5 to about 30 percent by weight, and in one embodiment from about 0.5 to about 25 percent by weight, and in one embodiment in the range of from about 1 to about 20 percent by weight.

The membrane disrupting agent may comprise one or more lipid structure disrupting agents, glucose scaffolding/membrane disrupting agents, or a mixture of two or more thereof. While not wishing to be bound by theory, it is believed that the membrane disrupting agent may render the prions more susceptible to proteolytic cleavage with the prion deactivating enzyme. The lipid structure disrupting agents may comprise one or more lipase enzymes. The lipase enzymes that may be used may include those available from Novozymes under the tradenames Lipolase and Lipex; those available from Genencor under the tradename Lipolax Ultra; and those available from Enzyme Solutions Pty Ltd. under the tradename G-Zyme G999. The glucose scaffolding/membrane disrupting agents that may be used may include one or more enzymes such as glycosidases (e.g., Lysozyme), glucoseoxidases, amylases, cellulases, mannases, β-glucanases, mixtures of two or more thereof, and the like. The membrane disrupting agent may be present in the inventive prion deactivating composition at a concentration in the range up to about 30 percent by weight, and in one embodiment from about 1 to about 30 percent by weight, and in one embodiment from about 3 to about 20 percent by weight.

The activity enhancing agent may be used for enhancing or increasing the activity of the prion deactivating enzyme. The activity enhancing agent may be selected based on the prion deactivating enzyme or enzymes employed in the prion deactivating composition. The activity enhancing agent may function as a stabilizer for the active site of the enzyme. The activity enhancing agent may comprise calcium ions or salts thereof. The activity enhancing agent may comprise calcium chloride. The concentration of the activity enhancing agent that may be present in the prion deactivating composition may be selected as desired to provide a particular or desired level of enzyme activity. The activity enhancing agent may be present in the prion deactivating composition at a concentration up to about 1 percent by weight, and in one embodiment in the range of from about 0.01 to about 1 percent by weight, and in one embodiment in the range from about 0.01 to about 0.8 percent by weight, and in one embodiment from about 0.05 to about 0.5 percent by weight.

The cosolvent may comprise one or more polyols containing only carbon, hydrogen, and oxygen atoms. The cosolvent may comprise one or more $C_2$ to $C_6$ polyols, such as 1,2-propanediol, 1,2-butanediol, hexylene glycol, glycerol, sorbitol, mannitol, and glucose. Higher glycols, polyglycols, polyoxides and glycol ethers may also be used as co-solvents. The cosolvent may comprise one or more alkyl ether alcohols such as methoxyethanol, methoxyethanol acetate, butyoxyethanol (butyl cellosolve), propylene glycol, polyethylene glycol, polypropylene glycol, diethylene glycol monoethyl ether, diethylene glycol monopropyl ether, diethylene glycol monobutyl ether, tripropylene glycol methyl ether, propylene glycol methyl ether, dipropylene glycol methyl ether, propylene glycol methyl ether acetate, dipropylene glycol methyl ether acetate, ethylene glycol n-butyl ether, 1,2-dimethoxyethane, 2-ethoxy ethanol, 2-ethoxy-ethylacetate, phenoxy ethanol, ethylene glycol n-propyl ether, and the like. Mixture of two or more of the foregoing cosolvents may be used. The cosolvent may be present in the prion deactivating composition at a concentration in the range up to about 50 percent by weight, and in one embodiment at a concentration in the range from about 5 to about 50 percent by weight, and in one embodiment at a concentration in the range from about 5 to about 40 percent by weight, and in one embodiment at a concentration in the range from about 10 to about 35 percent by weight.

The surfactant may comprise one or more anionic, cationic, non-ionic, and/or zwitterionic surfactants. The surfactant may have a hydrophilic lipophilic balance (HLB) in the range from about 1 to about 30, and in one embodiment in the range from about 3 to about 25. The surfactant may comprise one or more amine oxides, block copolymers of ethylene oxide and propylene oxide, phosphate esters, alkypolyglucosides, alcohol alkoxylates (e.g., alcohol ethoxylates), dodecylbenzene sulfonic acid, sodium 1-octane sulfonate, mixtures two or more thereof, and the like. The surfactant may comprise one or more sulfates, sulfonates (e.g., $C_{14}$-$C_{18}$ sulfonates), sulfonic acids, ethoxylates, sarcosinates, sulfosuccinates, or a mixture of two or more thereof. These may include sodium lauryl ether sulfate, triethanolamine lauryl sulfate, magnesium lauryl sulfate, sulfosuccinate esters, ammonium lauryl sulfate, alkyl sulfonates, sodium lauryl sulfate, sodium alpha olefin sulfonates, alkyl sulfates, sulfated alcohol ethoxylates, sulfated alkyl phenol ethoxylates, sodium xylene sulfonate, alkylbenzene sulfonates, triethanolamine dodecylbenzene sulfonate, sodium dodecylbenzene sulfonate, calcium dodecylbenzene sulfonate, xylene sulfonic acid, dodecylbenzene sulfonic acid, N-alkoyl sarcosinates, sodium lauroyl sarcosinate, dialkylsulfosuccinates, N-alkoyl sarcosines, lauroyl sarcosine, or a mixture of two or more thereof. The surfactant may comprise octyldimethylamine oxide, decyldimethylamine, dodecyldimethylamine, or a mixture of two or more thereof. An amphoteric surfactant that may be used is Mackam ODP-45M which is available from McIntyre and is identified as being disodiumethylhexyliminodiproprionate. A nonionic surfactant that may be used is Berol 508 which is available from Akzo-Nobel and is identified as an ethoxylated alcohol. The surfactant may be present in the prion deactivating composition at a concentration in the range up to about 40 percent by weight, and in one embodiment at a concentration in the range from about 1 to about 40 percent by weight, and in one embodiment at a concentration in the range from about 1 to about 30 percent by weight, and in one embodiment at a concentration in the range from about 2 to about 25 percent by weight.

The coupling agent may comprise one or more anionic couplers such as sodium xylene sulfonate or sodium cumene sulfonate; one or more nonionic couplers such as amine oxides and alkyl polyglucosides and their derivatives; one or more amphoteric couplers such as disodium ethylhexyliminodipropionate; one or more cationic coupling agents; or a mixture of two or more thereof. The coupling agent may be present in the inventive prion deactivating composition at a concentration in the range up to about 40 percent by weight, and in one embodiment in the range from about 1 to about 40 percent by weight, and in one embodiment in the range from about 1 to about 35 percent by weight, and in one embodiment at a concentration in the range from about 1 to about 30 percent by weight, and in one embodiment at a concentration in the range from about 2 to about 25 percent by weight.

The corrosion inhibitor may comprise one or more of Irgacor L190, Irgacor L190 Plus, Irgamet 42, CarboShield 1000, or a mixture of two or more thereof. Irgacor L190, Irgamet 42 and Carbo Shield 1000 are described above. Irgacor L190 Plus is 2,4,6-tri-(6-aminocaproic acid)-1,3,5-triazine which is available from Ciba. The corrosion inhibitor may comprise one or more azoles. The azoles may include the triazoles, such as benzotriazole, tolyltriazole, carboxybenzotriazole, mixtures of two or more thereof, and the like. Salts of the triazoles such as sodium tolyltriazole may be used. Salts of didecyldimethylammonium with tolyltriazole, benzotriazole, carboxybenzotriazole, ethanol-2,2'-[[methyl-1H-benzotriazol-1-yl)methyl]imino]bis-, mixtures of two or more thereof, and the like, may be used. Complexing agents which contribute to corrosion prevention may be used as corrosion inhibitors, complexing agents or both. The complexing agents that may be used may include Octaquest A65, Trilon M, Baypure CX100, Dissolvine GL, HEDP, salts of HEDP, ATMP, salts of ATMP, DTPMPA, salts of DTPMPA, EDDS, or a mixture of two or more thereof. The corrosion inhibitor may be present in the inventive prion deactivating composition at a concentration in the range up to about 40 percent by weight, and in one embodiment in the range from about 1 to about 40 percent by weight, and in one embodiment in the range from about 1 to about 30 percent by weight, and in one embodiment in the range from about 2 to about 25 percent by weight.

The oxidizing agent may comprise one or more of hydrogen peroxide; chlorine dioxide; peroxide generating salts such as salts of percarbonate, perborate, permanganate or a mixture of two or more thereof; per-acids such as peracetic acid and the like; or a mixture of two or more thereof. The oxidizing agent may be present in the inventive prion deactivating composition at a concentration in the range up to about 10 percent by weight, and in one embodiment in the range from about 0.1 to about 10 percent by weight, and in one embodiment in the range from about 0.2 to about 8 percent by weight, and in one embodiment in the range from about 0.5 to about 7 percent by weight.

The reducing agent may comprise one or more of thiols, phosphines, phosphites or a mixture of two or more thereof. The reducing agent may be present in the inventive prion deactivating composition at a concentration in the range up to about 10 percent by weight, and in one embodiment in the range from about 0.1 to about 10 percent by weight, and in one embodiment in the range from about 0.2 to about 8 percent by weight, and in one embodiment in the range from about 0.5 to about 7 percent by weight.

The acid may comprise one or more of phosphoric acid; nitric acid; boric acid; and/or one or more organic acids such as acetic acid, citric acid, glycolic acid and/or salicylic acid; or a mixture of two or more thereof. The acid may be present in the inventive prion deactivating composition at a concentration in the range up to about 10 percent by weight, and in one embodiment in the range from about 0.1 to about 10 percent by weight, and in one embodiment in the range from about 0.1 to about 8 percent by weight, and in one embodiment in the range from about 0.2 to about 6 percent by weight.

The defoamer may comprise one or more silicon compounds such as silica dispersed in polydimethylsiloxane. The defoamer may comprise one or more fatty amides, hydrocarbon waxes, fatty acids, fatty esters, fatty alcohols, fatty acid soaps, ethoxylates, mineral oils, polyethylene glycol esters, polyoxytheylene-polyoxpropylene block copolymers, alkyl phosphate esters such as monostearyl phosphate, or a mixture of two or more thereof. The defoamer may be in the form of a silicone containing solution or emulsion. The defoamer may be present in the inventive prion deactivating composition at a concentration in the range up to about 10 percent by weight, and in one embodiment in the range from about 0.001 to about 5 percent by weight, and in one embodiment in the range from about 0.005 to about 3 percent by weight.

The prion deactivating composition may have a pH with a sufficiently reduced alkalinity so as not to damage instruments or articles being treated or adversely affect enzyme stability. In addition to selection of a particular enzyme, the pH of the prion deactivating composition may be controlled by adjusting other factors including enzyme concentration, temperature, and/or type and/or concentration of activity enhancing agents. The prion deactivating composition may have a pH that is suitable for the prion deactivating enzyme to sufficiently deactivate the prion material. The pH of the prion deactivating composition may be selected based on the prion deactivation enzyme or enzymes employed in the composition. The prion deactivating enzymes may have sufficient activity only within a certain pH range or at a particular pH. The prion deactivating composition may have a pH in the range from about 7 to about 12, and in one embodiment in the range from about 7 to about 11, and in one embodiment in the range from about 7 to about 10, and in one embodiment in the range from about 7 to about 9.

The prion deactivating composition may be formed by mixing the various components in a suitable diluent or solvent, such as water. In one embodiment, the prion deactivating composition may be provided as a pre-mixed composition comprising all the ingredients, including the prion denaturing agent and the prion deactivating enzyme. In one embodiment, the prion deactivating composition may be provided as two separate compositions or solutions, wherein one composition comprises the prion denaturing agent, and the other composition comprises the prion deactivating enzyme. The separate compositions may then be combined prior to use in a cleaning, decontamination and/or sterilization process. When the prion denaturing agent and prion deactivating enzyme are provided as separate compositions or solutions, the compositions or solutions may be provided separately or as part of a kit.

The inventive prion deactivating composition may be diluted in a suitable solvent or diluent. The solvent or diluent may comprise water. The water may be potable from any municipality or natural source. The water may be deionized or purified using osmosis or distillation. The water may comprise soft water. The concentration of the inventive prion deactivating composition in the diluent may be at any desired level, for example, in the range from about 1/40 oz/gal (fluid ounces of prion deactivating composition per gallon of diluent) to about 1/10 oz/gal. The concentration of the inventive prion deactivating composition in the diluent may be in the range up to about 20% by weight, and in one embodiment in the range from about 0.001 to about 20% by weight, and in one embodiment in the range from about 0.001 to about 10% by weight, and in one embodiment in the range from about 0.1 to about 5% by weight, and in one embodiment in the range from about 0.1 to about 4% by weight, and in one embodiment in the range from about 0.1 to about 3.5% by weight, and in one embodiment in the range from about 0.1 to about 3.2% by weight, and in one embodiment in the range from about 0.1 to about 3% by weight, and in one embodiment in the range from about 0.1 to about 2.5% by weight, and in one embodiment in the range from about 0.1 to about 2% by weight. As such, the concentration of the prion denaturing agent and the concentration of the prion deactivating enzyme in the diluted prion deactivating composition will be correspondingly reduced. For example, a prion deactivating composition that contains 0.5% by weight prion denaturing agent which is diluted to 1 oz/gal (0.8% by weight) in water has a prion denaturing agent concentration of 40 parts per million (ppm). The concentration of solvent or diluent in the diluted inventive prion deactivating composition may be in the range up to about 99.99% by weight, and in one embodiment in the range from about 0.01 to about 99.99% by weight, and in one embodiment in the range from about 10 to about 95% by weight, and in one embodiment in the range from about 15 to about 90% by weight.

The invention may also relate to a method or process for treating materials contaminated with infectious proteins using the inventive prion deactivating composition. The materials to be treated may include protein infected surfaces and/or articles, including prion infected surfaces and/or articles. This method may comprise contacting the infected material with the inventive prion deactivating composition. The prion deactivating composition may be applied to the material to be treated by any suitable method including coating, spraying, dipping, immersing, and the like. The temperatures may be in the range from about 20° C. to about 70° C., and in one embodiment in the range from about 30° C. to about 60° C. The material to be treated may be exposed to the prion deactivating composition for a period of time sufficient to deactivate infectious proteins (e.g., prions) on and/or in the material. This period of time may be in the range from about 1 minute to about 2 hours, and in one embodiment from about 5 minutes to about 1 hour. In one embodiment, the prion deactivating composition may be used at either a low concentration, a low temperature, or both low concentration and low temperature, and the contact time to deactivate the infectious proteins or prions may be relatively long, for example, about 2 hours or more, and in one embodiment from about 2 to about 20 hours, and in one embodiment from about 2 to about 10 hours, and in one embodiment from about 2 to about 5 hours.

The material which may be treated with the prion deactivating composition may include surfaces of instruments employed in medical, dental, and/or pharmaceutical procedures, as well as surfaces of equipment and work surfaces used in the food and beverage processing industry. These may include walls, floors, ceilings, fermentation tanks, fluid supply lines, and the like. The materials to be treated may include contaminated surfaces in hospitals, industrial facilities, research laboratories, and the like. The materials that may be treated may include: surfaces and articles involved with the treatment of medical waste, such as blood, tissue and other body waste, prior to disposal; rooms, cages, and the like used for housing animals known or suspected to be infected with prions; surfaces and articles relating to the decontamination of BSE infected areas, including slaughterhouses, food processing facilities, and the like; materials relating to medical device reprocessing, decontamination or disinfection; sterilization systems; surfaces and articles relating to the formulation of pharmaceuticals, medicaments, and cleaning agents having antifungal, antiviral, antituberculoidal, and/or antibacterial efficacy as well as anti-prion efficacy.

Optionally, after exposing the infected material to the prion deactivating composition, the material may be further subjected to additional cleaning operations. The additional cleaning operations may include sterilization operations. The sterilization operations may include liquid phase sterilization operations employing peracids (e.g., peracetic acid) and/or peroxides, and/or vapor phase sterilization operations employing, for example, peroxides such as hydrogen peroxide, and the like. The vaporous hydrogen peroxide may be used in combination with ammonia. Other oxidants such as hypochlorites, solutions of ozone, and the like, may be used.

The present invention may be further understood with reference to the following examples. The examples are intended to demonstrate more specific embodiments of the invention and are not intended to be limiting in any manner.

Example 1

The formulations identified in the table below are prion deactivating compositions within the scope of the invention. In the table below all numerical values are in percent by weight, with the exception that the numerical value for ethanolamine refers to the pH for the formulation achieved with the addition of a suitable amount of the ethanolamine. Each formulation is in soft water. The amount of soft water in each formulation is the amount needed to bring the formulation to a total of 100% by weight.

| | Weight % | | | | | | | | | | | |
|---|---|---|---|---|---|---|---|---|---|---|---|---|
| | A | B | C | D | E | F | G | H | I | J | K | L |
| Propylene glycol | 20 | 20 | 20 | 20 | 20 | 25 | 25 | 25 | 25 | 25 | 25 | 25 |
| Citric acid | 4 | 6 | 4 | 4 | 4 | 4 | 4 | 4 | 4 | 6 | 4 | 6 |
| Calcium chloride | 0.1 | 0.15 | 0.15 | 0.15 | 0.1 | 0.15 | 0.1 | 0.05 | 0.05 | 0.05 | 0.05 | 0.05 |
| $C_{9-11}$ Pareth-8 | 1 | 2 | 5 | 3 | 0 | 1 | 1 | 3 | 0 | 5 | 1 | 2 |
| $C_{12-13}$ Pareth-7 | 0 | 1 | 0 | 0 | 3 | 1 | 0 | 0 | 2 | 0 | 0 | 1 |
| Octyldimethylamine oxide | 1 | 2 | 3 | 3 | 0 | 3 | 1 | 2 | 3 | 2 | 0 | 1 |
| Decyldimethylamine oxide | 1 | 0 | 0 | 0 | 2 | 0 | 1 | 1 | 0 | 0 | 0 | 0 |
| Savinase Protease enzyme (subtillisin) | 4 | 4 | 0 | 4 | 8 | 2 | 4 | 0 | 2 | 2 | 4 | 0 |
| Alcalase Protease enzyme (subtillisin) | 4 | 4 | 8 | 4 | 0 | 2 | 0 | 4 | 2 | 2 | 0 | 4 |

-continued

| Component | | | | | | | | | | | | |
|---|---|---|---|---|---|---|---|---|---|---|---|---|
| 6,6'6''-(1,3,5-triazine-2,4,6-triyltriimino)tris(hexanoic acid) | 0 | 1 | 1 | 1 | 0 | 1 | 0 | 2 | 1 | 0 | 0 | 2 |
| Ethanolamine | Add to pH 8.00 | Add to pH 6.50 | Add to pH 7.00 | Add to pH 7.75 | Add to pH 7.50 | Add to pH 7.75 | Add to pH 8.50 | Add to pH 7.00 | Add to pH 7.00 | Add to pH 8.50 | Add to pH 6.50 | Add to pH 8.00 |
| Potassium Hydroxide (40%) | 0 | 1 | 1 | 0 | 0 | 0.5 | 1 | 0 | 0 | 2 | 1 | 3 |
| Meroxapol 252 (Propylene oxide/Ethylene oxide block copolymer) | 2 | 0 | 1 | 1.1 | 1.1 | 1.3 | 1.1 | 1.5 | 1.5 | 0 | 1.5 | 2 |
| Meroxapol 174 (Propylene oxide/Ethylene oxide block copolymer) | 0 | 2 | 1 | 0 | 0 | 0.5 | 1.3 | 1.1 | 0 | 1.5 | 0 | 0 |
| Sodium methylbenzotriazole (Sodium tolyltriazole 50%) | 0 | 1 | 1 | 1 | 0 | 0 | 2 | 0 | 0 | 0 | 0 | 0 |
| Sodium benzotriazole (50%) | 1 | 0 | 0 | 0 | 1 | 0 | 0 | 2 | 1.5 | 1 | 0 | 0 |
| Fragrance | 0.1 | 0.1 | 0.1 | 0.08 | 0.1 | 0.1 | 0.1 | 0.1 | 0.1 | 0.05 | 0.05 | 0.08 |
| Ethylene oxide/propylene oxide block copolymer (1) | 0 | 1 | 1 | 0 | 0 | 2 | 0 | 1 | 1 | 1 | 2 | 2 |
| Ethylene oxide/propylene oxide block copolymer (2) | 2 | 1 | 2 | 2 | 1 | 0 | 1 | 0 | 0 | 0 | 0 | 0 |
| Tetrasodium Iminodissuccinate | 0 | 1 | 0 | 0 | 1 | 0 | 0 | 0 | 0 | 0 | 1 | 3 |
| Tetrasodium Ethylenediaminedisuccinate | 0 | 0 | 1 | 0 | 1 | 1 | 1 | 0 | 0 | 0 | 1 | 0 |
| Dimethyldidecyl ammonium carbonate/bicarbonate | 2 | 0 | 1.5 | 1.5 | 1 | 1 | 0 | 2 | 1.5 | 2 | 1.5 | 2 |
| 10% Silicone emulsion | 0.1 | 0.1 | 0.1 | 0.025 | 0 | 0.1 | 0.1 | 0.05 | 0.1 | 0.1 | 0.05 | 0.1 |

| | Weight % | | | | | | | | | |
|---|---|---|---|---|---|---|---|---|---|---|
| | M | N | O | P | Q | R | S | T | U | V |
| Propylene glycol | 25 | 15 | 15 | 15 | 15 | 15 | 15 | 10 | 10 | 10 |
| Citric acid | 4 | 2 | 2 | 1 | 1 | 3 | 4 | 6 | 4 | 2 |
| Calcium chloride | 0.05 | 0.15 | 0.15 | 0.1 | 0.05 | 0.1 | 0.15 | 0.2 | 0.15 | 0.1 |
| $C_{9-11}$ Pareth-8 | 4 | 0 | 1 | 1 | 3 | 3 | 1 | 1.5 | 3 | 5 |
| $C_{12-13}$ Pareth-7 | 0 | 4 | 1 | 1 | 1 | 1 | 3 | 1.5 | 0 | 0 |
| Octyldimethylamine oxide | 1 | 0 | 3 | 0 | 0 | 0 | 1 | 2 | 1 | 0 |
| Decyldimethylamine oxide | 0 | 0 | 0 | 3 | 0 | 1 | 0 | 0 | 0 | 1 |
| Savinase Protease enzyme (subtillisin) | 2 | 2 | 4 | 4 | 2 | 3 | 3 | 0 | 0 | 4 |
| Alcalase Protease enzyme (subtillisin) | 2 | 2 | 0 | 0 | 2 | 1 | 1 | 4 | 4 | 0 |
| 6,6'6''-(1,3,5-triazine-2,4,6-triyltriimino)tris(hexanoic acid) | 1 | 0 | 2 | 2 | 1 | 0 | 1 | 0 | 0.5 | 0.5 |
| Ethanolamine | Add to pH 8.00 | Add to pH 7.25 | Add to pH 7.75 | Add to pH 7.25 | Add to pH 8.00 | Add to pH 6.50 | | Add to pH 8.50 | Add to pH 6.75 | Add to pH 8.25 |
| Potassium Hydroxide (40%) | 0 | 0 | 0.2 | 0 | 0 | 0.5 | 0.5 | 2 | 1 | 0 |
| Meroxapol 252 (Propylene oxide/Ethylene oxide block copolymer) | 0 | 3 | 1.1 | 0 | 2 | 1.3 | 1.5 | 0 | 0 | 2 |
| Meroxapol 174 (Propylene oxide/Ethylene oxide block copolymer) | 2 | 0 | 0 | 1.1 | 0 | 0.3 | 0 | 2 | 1 | 0 |
| Sodium methylbenzotriazole (Sodium tolyltriazole 50%) | 0 | 1 | 0 | 0 | 1 | 1 | 2 | 1.5 | 0.5 | 0 |
| Sodium benzotriazole (50%) | 1 | 0 | 1 | 1 | 0 | 0 | 0 | 0 | 0.5 | 1 |
| Fragrance | 0.025 | 0.025 | 0.05 | 0.05 | 0.08 | 0.025 | 0.025 | 0.1 | 0.05 | 0.1 |
| Ethylene oxide/propylene oxide block copolymer (1) | 2 | 1 | 0 | 0 | 0 | 1 | 1 | 0 | 0 | 0 |
| Ethylene oxide/propylene oxide block copolymer (2) | 0 | 1 | 1 | 2 | 3 | 1 | 0 | 0 | 0 | 0 |
| Tetrasodium Iminodissuccinate | 0 | 2 | 0 | 1 | 0 | 0 | 0 | 0 | 0 | 2 |
| Tetrasodium Ethylenediaminedisuccinate | 3 | 0 | 0 | 0 | 2 | 0 | 0 | 0 | 1 | 0 |
| Dimethyldidecyl ammonium carbonate/bicarbonate | 2 | 0 | 1.5 | 1 | 2 | 0.5 | 0 | 0.5 | 1 | 2 |
| 10% Silicone emulsion | 0.1 | 0.025 | 0 | 0 | 0.075 | 0 | 0.1 | 0.1 | 0.1 | 0.1 |

Propylene glycol is believed to function as a preservative and to reduce water activity.

Citric acid is used to adjust the pH of the formulation.

Calcium chloride is believed to function as an activity enhancing agent.

$C_{9-11}$ Pareth-8 is a biodegradable, linear primary alcohol exthoxylate with 8 moles of ethoxylation. This material, which is a nonionic surfactant with an HLB value of 13.9, is available from Tomadol as Tomadol 91-8. This material is believed to provide wetting, emulsification/solubilization and low foaming characteristics.

$C_{12-13}$ Pareth-7 is a biodegradable, linear primary alcohol ethoxylate with 7 moles of ethoxylation. This material, which is a nonionic surfactant with an HLB value of 12, is available from Tomah as Tomadol 23-6.5. This material is believed to provide wetting and emulsification/solubilization characteristics.

Octyldimethylamine oxide is a nonionic surfactant that is believed to provide wetting and low foaming characteristics as well as hydrotrophic benefits. This material is available from McIntyre under the name Mackamine C-8.

Decyldimethylamine oxide is a nonionic surfactant that is believed to provide wetting and low foaming characteristics as well as hydrotrophic benefits. This material is available from McIntyre under the name Mackamine C-10.

Savinase® protease enzyme (subtilisin 309) is a non-specific serine protease produced by a genetically modified Bacillus. This material is available from Novozymes under the name Savinase® 16.0L, Type EX.

Alcalase protease enzyme (subtilisin) is a non-specific protease produced by *Bacillus lichenformis*. This enzyme contains a stabilization package (4-formylphenylboronic acid) which is believed to provide enhanced enzyme stability. This material is available from Novozymes under the name Alcalase Ultra 2.5L.

6,6',6''-(1,3,5-triazine-2,4,6-triyltriimino)tris(hexanoic acid) is an organic polycarboxylic acid that is believed to function as a copper (II) complexing agent and as a corrosion inhibitor for soft metals, such as aluminum and anodized aluminum. This material is available from Ciba as Irgacor L-190.

Ethanolamine is believed to function as an alkalinity and amine source to solublize the polycarboxylic acid. This material may enhance soft metal corrosion inhibition. This material may neutralize the citric acid and provide a buffer system for the formulation.

Potassium hydroxide is used to adjust the pH of the formulation.

Meroxapol 252 is a biodegradable block copolymer of propylene oxide and ethylene oxide which is believed to provide oil emulsification and defoaming characteristics. This material is a surfactant which has an HLB value of 4. This material is available from BASF under the name Pluronic 25R2.

Meroxapol 174 is a biodegradable block copolymer of propylene oxide and ethylene oxide which is believed to provide oil emulsification and defoaming characteristics. This material is a surfactant which has an HLB value of 12. This material is available from BASF under the name Pluronic 17R-4.

Sodium methylbenzotriazole (sodium tolyltriazole) is believed to function as a copper (II) complexing agent and provide corrosion inhibition for soft metals such as copper and brass. The alkalinity from this material is believed to aid in solubilizing the polycarboxylic acid.

Sodium benzotriazole is believed to function as a copper (II) complexing agent and provide corrosion inhibition for soft metals such as copper and brass. The alkalinity from this material is believed to aid in solubilizing the polycarboxylic acid.

The fragrance identified in the table above may be any fragrance suitable to a water and propylene glycol solubility system. A fragrance that may be used is Fragrance Chemia #33498 from Chemia Corporation.

The ethylene oxide/propylene oxide block copolymer (1) is a biodegradable, block copolymer of ethylene oxide and propylene oxide that has an HLB value of 2. This material is believed to provide soil emulsification, detergency and foam control characteristics. This material is available from Dow Chemical as Tergitol L-81.

The ethylene oxide/propylene oxide block copolymer (2) is a biodegradable, block copolymer of ethylene oxide and propylene oxide that has an HLB value of 7. This material is believed to provide soil emulsification, detergency and foam control characteristics. This material is available from Dow Chemical as Tergitol L-62.

Tetrasodium iminodisuccinate is a biodegradable chelant which may act as a copper (II) complexing agent and may provide corrosion inhibition for soft and ferrous metals. The alkalinity of this material is believed to aid in solubilizing the polycarboxylic acid.

Tetrasodium ethylenediaminedisuccinate is a biodegradable chelant which may act as a copper (II) complexing agent and may provide corrosion inhibition for soft and ferrous metals. The alkalinity of this material is believed to aid in solubilizing the polycarboxylic acid.

The dimethyldidecyl ammonium carbonate/bicarbonate is believed to function as a copper (II) complexing agent and provide corrosion inhibition for soft metals such as aluminum and anodized aluminum. This material, which is a quaternary amine with a carbonate/bicarbonate counter ion, is available from Lonza Incorporated as CarboShield 1000.

The 10% silicone emulsion, which is believed to function as a silicone based defoamer, is available from Dow Corning under the name Dow Corning DSP Antifoam Emulsion.

In the following examples, western blot tests are used to evaluate the effectiveness of the indicated prion deactivating compositions against prion infected material. The western blot test, which may be referred to as an immunoblot test, is a method that is used to detect a specific protein in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane where they are probed (detected) using antibodies specific to the target protein. The probes are labeled and bound to the protein of interest. Size approximations are taken by comparing stained bands to that of a marker or ladder loaded during electrophoresis.

Example 2

The following composition is used to provide the base formulation for Examples 2A and 2B. Sodium tolyltriazole, which is believed to function as a complexing agent, is at a relatively low concentration level.

|  | Parts by Weight |
|---|---|
| Soft water | 198.31 |
| Potassium hydroxide | 24.00 |

-continued

|  | Parts by Weight |
|---|---|
| Citric acid | 8.01 |
| Propylene glycol | 112.07 |
| Sodium borate | 13.05 |
| Calcium chloride | 0.20 |
| C9-11 Pareth-8 | 20.73 |
| Sodium tolyltriazole | 0.41 |
| Total | 398.00 |

Example 2A

The composition from Example 2 (200.09 grams) is mixed with potassium hydroxide (0.22 gram). The pH of the resulting base formulation is 10.00.

Example 2B

The composition from Example 2 (197.91 grams) is mixed with potassium hydroxide (0.76 gram). The pH of the resulting base formulation is 12.00.

Example 3

The following composition is prepared. Sodium tolyltriazole is at a relatively high concentration as compared to Example 2.

|  | Parts by Weight |
|---|---|
| Soft water | 330.60 |
| Triethanolamine | 108.02 |
| Citric acid | 36.04 |
| Propylene glycol | 252.10 |
| Sodium borate | 29.50 |
| C9-11 Pareth-8 | 45.12 |
| Sodium tolyltriazole | 9.05 |
| Total | 807.58 |

This composition (180.92 grams) is mixed with calcium chloride (0.34 gram), soft water (19.68 grams), and potassium hydroxide (19.91 grams). The pH of the resulting base formulation is 11.00.

Example 4

The following composition is prepared.

|  | Parts by Weight |
|---|---|
| Soft water | 330.53 |
| Triethanolamine | 107.99 |
| Citric acid | 36.15 |
| Propylene glycol | 251.96 |
| Sodium borate | 29.37 |
| C9-11 Pareth-8 | 45.01 |
| Benzotriazole | 9.10 |
| Total | 807.44 |

This composition (180.26 grams) is mixed with soft water (19.75 grams) and potassium hydroxide (22.05 grams). The pH of the resulting base formulation is 11.00.

Example 5

A strain of prions in infected brain homogenates is tested. The strain is laboratory strain 263K (scrapie strain adapted to hamster). The base formulations from Examples 2A, 2B, 3 and 4 are used. 1.5 ml of each base formulation is added to 48.5 ml of water and heated to 55° C. 64 microliters of enzyme or water (control) are added to each formulation. 80 microliters of the formulation are removed and 20 microliters of brain homogenate are added. The resulting mixtures are mixed and used to conduct western blot tests. For each western blot test, a sample corresponding to 1 mg is loaded on a SDS-PAGE gel (12% polyacrylamide) and electroblotted onto a nitrocellulose membrane. The prion protein is detected with mouse monoclonal antibody SAF-60 raised against hamster PrP codon 157-161 (from the CEA-SPI, Saclay, France), followed by a peroxidase-conjugated goat anti-mouse antibody. Immunoreactivity is visualized by chemiluminescence and detected by standard autoradiography.

The test results provided in FIG. 1 show the benefit of the Savinase protease enzyme over the other enzymes tested (i.e., an experimental enzyme, Alcalase, Everlase, Purafect ox and Properase). The base formulations tested are from Examples 2A, 2B, 3 and 4. The negative control is for 20% healthy hamster brain homogenate. The positive control is for 20% diseased (236K) hamster brain homogenate. The positive control 1:5 is for a 1:5 dilution of the 20% diseased brain homogenate. The enzyme exposure time is 30 minutes. The film exposure time is 1 minute. Without enzyme there is no effect for the formulations tested. There are varying levels of efficacy for the enzymes when combined with the base formulations, with significant effectiveness shown by the Savinase protease enzyme.

The tests reported in FIG. 2 employ the SAF-60 antibody (core of the protein). The base formulation tested is from Example 4. The negative control is for 20% healthy hamster brain homogenate. The positive control is for 20% diseased (236K) hamster brain homogenate. The positive control 1:5 is for a 1:5 dilution of the 20% diseased brain homogenate. The film exposure time is either 1 minute or 5 minutes. The results indicate that the Savinase protease enzyme by itself does not have the degradatory activity level of the enzyme when used in the base formulation of Example 4.

FIG. 3 shows results when employing the 3F4 antibody (just before core of protein). The base formulation tested is from Example 4. The negative control is for 20% healthy hamster brain homogenate. The positive control is for 20% diseased (236K) hamster brain homogenate. The positive control 1:5 is for a 1:5 dilution of the 20% diseased brain homogenate. The film exposure time is either 1 minute or 5 minutes. The results indicate that the Savinase protease enzyme by itself does not have the activity level of the enzyme when used in the base formulation from Example 4.

The test results reported in FIG. 4 show the effect of increasing amounts of the Savinase protease enzyme (16 to 64 microliters) at two levels (0.5 mL and 1.5 mL) of the base formulation from Example 4. The numerical values 16, 32 and 64 in FIG. 4 refer to microliters of the Savinase protease enzyme. The negative control is for 20% healthy hamster brain homogenate. The positive control is for 20% diseased (236K) hamster brain homogenate. The positive control 1:5 is for a 1:5 dilution of the 20% diseased brain homogenate. The enzyme exposure time is 30 minutes. The film exposure time is 1 minute. The results indicate that the enzyme performs better with increasing amounts of the base formulation.

The results reported in FIG. 5 are at film exposure times of 5 minutes. These results show that the formulations from Examples 2A and 2B with relatively low levels of complexing agent (i.e., sodium tolyltriazole) have similar activities at pH 10 (Example 2A) and pH 12 (Example 2B) over 30 minutes of contact time. The negative control is for 20% healthy hamster brain homogenate. The positive control is for 20% diseased (236K) hamster brain homogenate. The positive control 1:5 is for a 1:5 dilution of the 20% diseased brain homogenate. After 1 hour of contact time the pH 10 formulation shows greater cleaving of the prion protein than the pH 12 formulation. The same effect of better activity at 1 hour then 30 minutes is demonstrated for the pH 11 samples (Examples 3 and 4) with relatively high levels of complexing agents (i.e., sodium tolyltriazole in Example 3 and benzotriazole in Example 4).

Example 6

The following base formulation is prepared.

|  | Parts by Weight |
| --- | --- |
| Potassium hydroxide | 7 |
| Triethanolamine | 12 |
| Citric acid | 4 |
| Propylene glycol | 28 |
| Sodium borate | 3.27 |
| Calcium chloride | 0.16 |
| C9-11 Pareth-8 | 5 |

Figure 6:
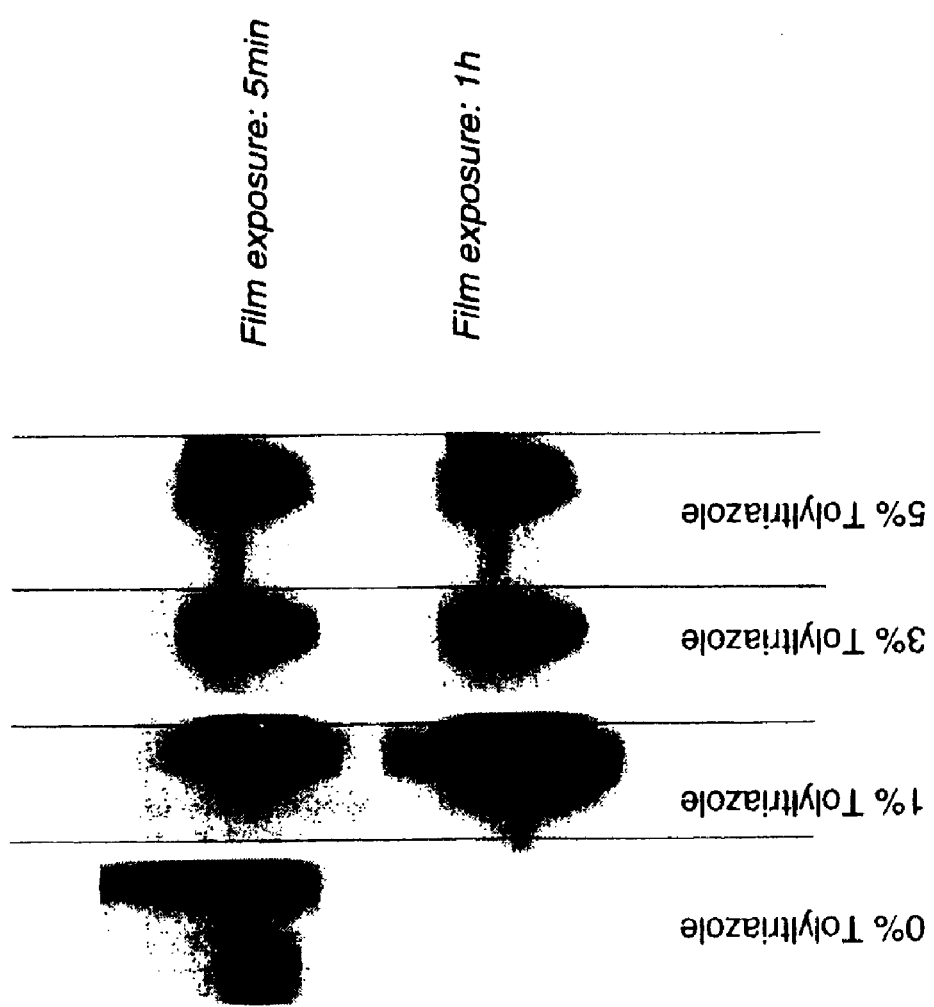
FIG. 6 shows western blot test results for the tests reported in Example 6.

The base formulation (60 microliters) is mixed with water (2.0 ml) and heated to 55° C. This formulation has a pH of 9. 8 microliters of Savinase protease enzyme or water (control) are added. 80 microliters of the resulting formulation are removed and 20 microliters of the brain homogenate referred to in Example 5 are added. The resulting mixture is mixed and exposed for a contact time of 30 minutes. Western blot tests are conducted. The western blot test results are shown in FIG. 6. In FIG. 6, the left side in each line (labeled 0% tolyltriazole, 1% tolyltriazole, etc.) is for the test with enzyme, and the right side in each lane is for the test without enzyme. The results show the benefit of adding tolyltriazole to the base formulation with increased effect at all concentrations, with the effect 3% being particularly advantageous. In FIG. 6 film exposure times of 5 minutes and 1 hour are shown. Two channels per column are shown, the left side being with enzyme and the right side being without enzyme. The results indicate that a concentration of 1% tolyltriazole improves efficacy dramatically. At 3% tolyltriazole, the protein is completely destroyed. The effect at 5% tolyltriazole is somewhat decreased as compared to 3% tolyltriazole.

Example 7

The following base formulation is prepared.

|  | Parts by Weight |
| --- | --- |
| Potassium hydroxide | 7 |
| Triethanolamine | 12 |
| Citric acid | 4 |
| Propylene glycol | 28 |
| Sodium borate | 3.27 |
| Calcium chloride | 0.16 |
| Tergitol 15-S-7 (secondary alcohol ethoxylate from Dow) | 10 |
| Benzotriazole | 1 |

Figure 7:
FIG. 7 shows western blot test results for the tests reported in Example 7.

The base formulation (60 microliters) is mixed with water (2.0 ml) and heated to 55° C. 8 microliters of Savinase protease enzyme or water (control) are added. 80 microliters of the resulting formulation are removed and 20 microliters of the brain homogenate referred to in Example 5 are added. The resulting mixture is mixed and exposed for a contact time of 30 minutes. Western blot tests are conducted with the results shown in FIG. 7. In FIG. 7, the left side in each lane (the planes being labeled pH 8.0, pH 8.5 and pH 9.0) is for the test using enzyme, and the right side in each lane is for the test without enzyme. These results show the pH dependent activity of the base formulation with 1% benzotriazole. The activity at pH of 8.5 and 8.0 is less than at a pH of 9.0.

Example 8

The following base formulation is prepared.

|  | Parts by Weight |
| --- | --- |
| Potassium hydroxide | 7 |
| Triethanolamine | 12 |
| Citric acid | 4 |
| Propylene glycol | 28 |
| Sodium borate | 3.27 |
| C9-11 Pareth-8 | 5 |

Figure 8:
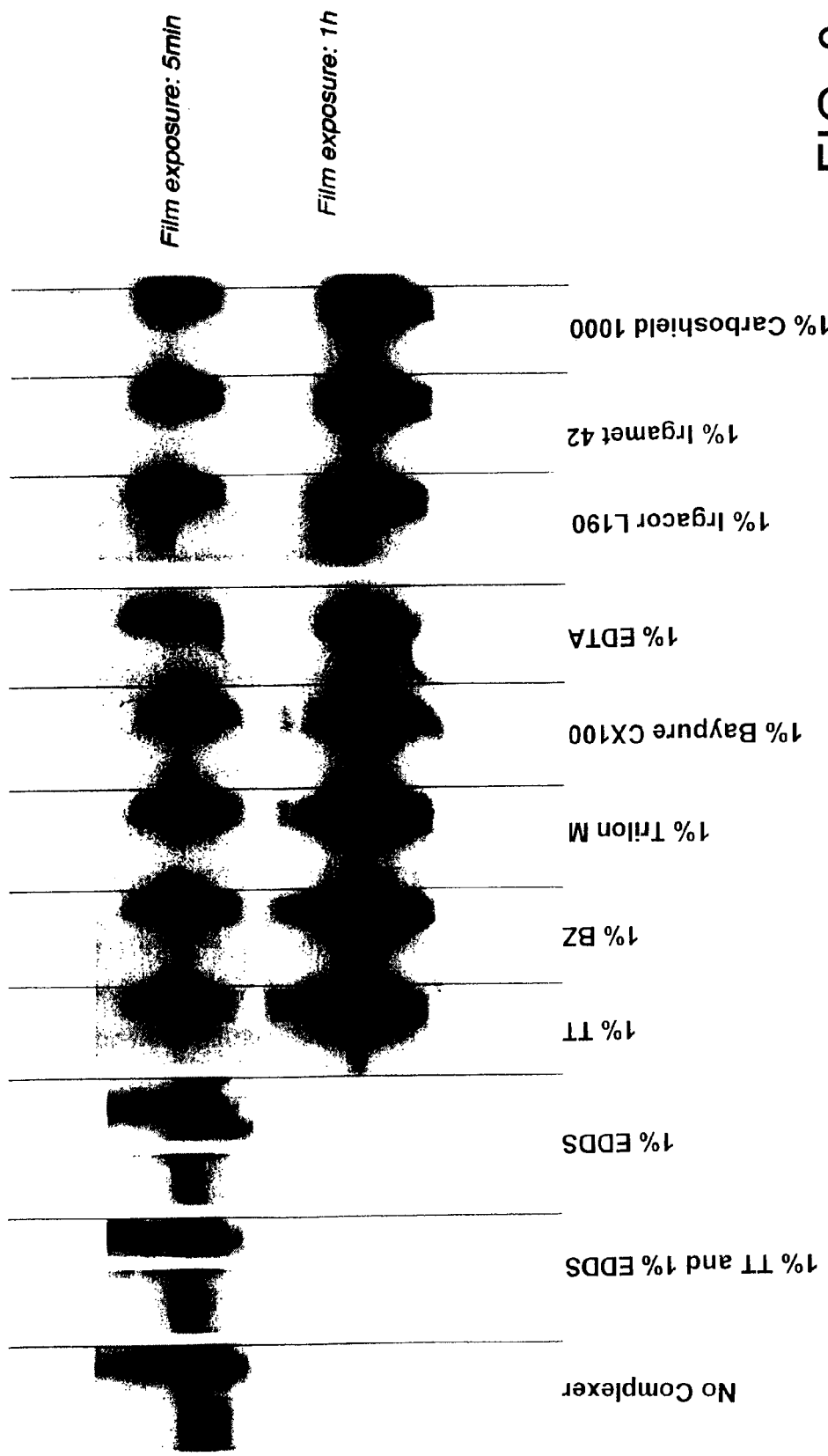
FIG. 8 shows western blot test results for the tests reported in Example 8.

The complexing agents shown in FIG. 8 are added to the base formulation at the concentration levels indicated in FIG. 8. In FIG. 8, the following abbreviations or tradenames are used:
  BZ: benzotriazole
  TT: tolyltriazole
  EDDS: ethylenediaminedisuccinic acid
  EDTA: ethylenediaminetetraacetic acid
  Trilon M: trisodiummethylglycine diacetic acid
  Baypure CX100: tetrasodiumtriiminodiscuccinic acid
  Irgacor L190: 6,6'6"-(1,3,5-triazine-2,4,6-triyltriimino) tris(hexanoic acid)
  Irgamet 42: ethanol-2,2'-[[methyl-1H-benzotriazol-1-yl) methyl]imino]bis-
  CarboShield 1000: didecyldimethyl ammonium carbonate/bicarbonate The formulations (60 microliters) shown in the first three columns on the left in FIG. 8 are each mixed with water (2.0 ml) and heated to 55° C. These formulations have a pH of 9. 8 microliters of Savinase protease enzyme or water (control) are added. 80 microliters of the formulations are removed and 20 microliters of the brain homogenate referred to in Example 5 are added. The resulting mixtures are exposed for contact times of 30 minutes. Western blot tests are performed and the results are shown in the first three columns on the left in FIG. 8. Film exposure times of 5 minutes and 1 hour are used. For each column in FIG. 8 there are two channels, the left side is with enzyme and the right side is without enzyme. In each case improvement is shown for the base formulation in combination with enzyme as compared to the base formulation without enzyme.

The base formulations (0.75 ml) shown in the eight columns on the right in FIG. 8 are each mixed with water (24.5 ml) and heated to 60° C. These formulations have a pH of 9. 115 microliters of Savinase protease enzyme or water (control) are added. 80 microliters of the formulation are removed and 20 microliters of the brain homogenate referred to in Example 5 are added. The resulting mixtures are exposed for contact times of 30 minutes. Western blot tests are performed and the results are shown in FIG. 8. In FIG. 8, the left side in each lane (labeled no complexer, 1% TT and 1% EDDS, etc.) is for the test using enzyme, and the right side in each lane is for the test without enzyme. In each case improvement is shown for the base formulation in combination with enzyme as compared to the base formulation without enzyme.

Example 9

Formulation D from the table in Example 1 is used as a Base Formulation. The following additive composition, which is identified in FIG. 9 as a "Booster," is combined with the Base Formulation at various concentration levels. The additive composition has the following formulation:

|  | Parts by Weight |
| --- | --- |
| Tetrasodium imminodisuccinate | 5.00 |
| Sodium tolyltriazole | 5.04 |
| Soft water | 90.03 |

The Base Formulation is dispersed in tap water at a concentration of 2% by weight and combined with the additive composition at concentrations ranging from 0% by weight to 2.5% by weight to provide samples with varying levels of pH as follows:

| Additive Composition | pH |
| --- | --- |
| 0% | 8.01 |
| 0.5% | 8.51 |
| 1% | 8.76 |
| 1.5% | 8.93 |
| 2.0% | 9.06 |
| 2.5% | 9.16 |

Figure 9:
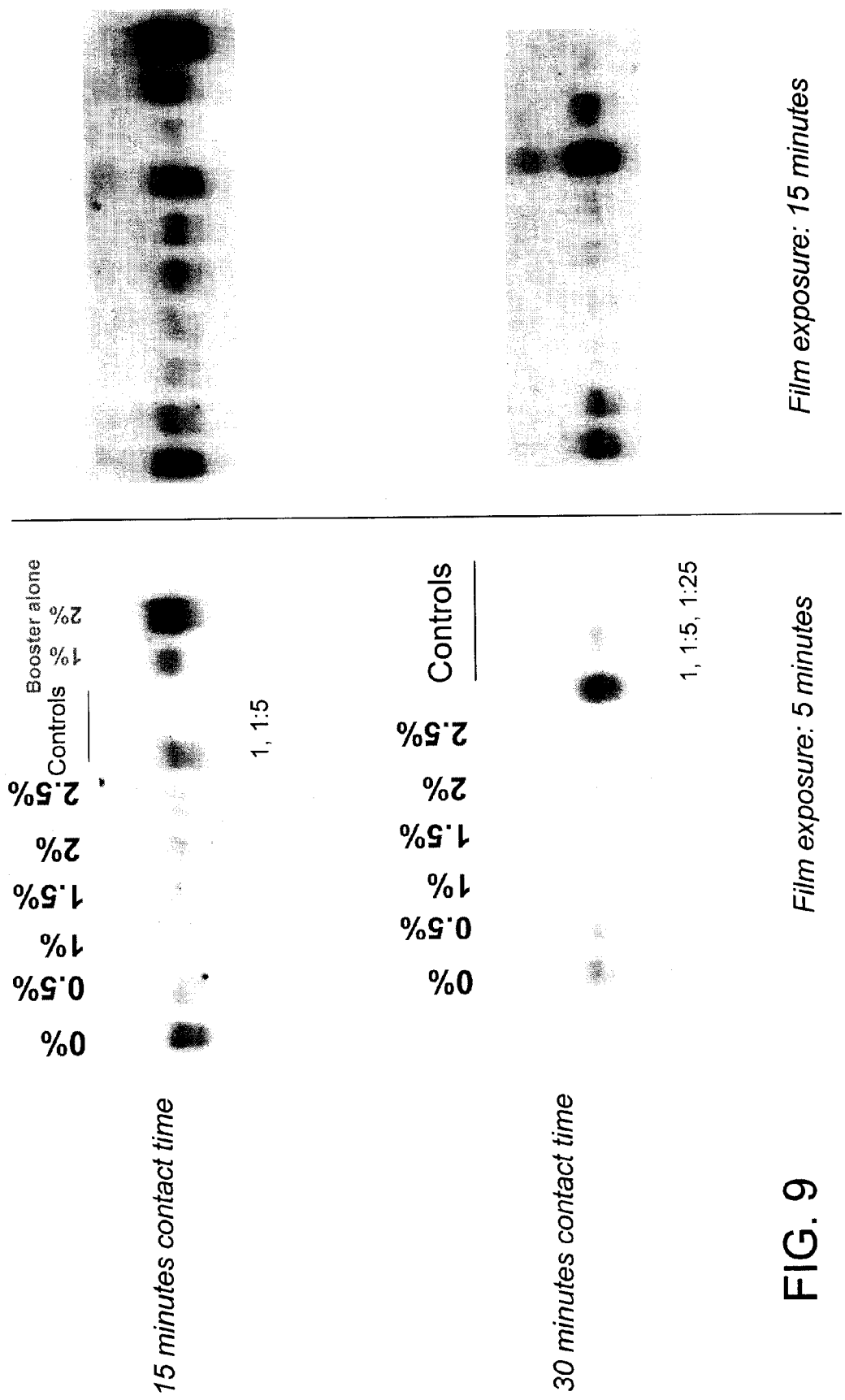
FIG. 9 shows western blot test results for the tests reported in Example 9.

The tap water has a pH of 7.76. Western blot tests are conducted using these samples and brain homogenate. The concentration of brain homogenate is 4% by weight. The final concentration of the Base Formulation after combining with the brain homogenate is 1.6% by weight. The base formulation (200 microliters) is mixed with tap water (10.0 ml) and heated to 55° C. 0.0 microliters (0.0%), 50 microliters (0.5%), 100 microliters (1.0%), 150 microliters (1.5%), 200 microliters (2.0%) or 250 microliters (2.5%) of the additive composition are added. 80 microliters of the resulting formulation are removed and 20 microliters of the 4% brain homogenate are added. The resulting mixture is mixed and exposed for a contact time of 15 or 30 minutes. Western blot tests are conducted with the results shown in FIG. 9. In FIG. 9, the "control 1" is for the 4% brain homogenate without the addition of the Base Formulation or additive composition. The "control 1:5" shown in FIG. 9 is for the 4% brain homogenate diluted in tap water at a weight ratio of 1 part of 4% brain homogenate to 5 parts of tap water. Similarly, the "control 1:25" is for the 4% brain homogenate diluted in tap water at a weight ratio of 1:25. The "Booster alone" is for the additive composition (or Booster) at a concentration of 1% by weight or 2% by weight as indicated in FIG. 9 without the Base Formulation.

Example 10

Example 9 is repeated except that deionized water is used instead of tap water. The Base Formulation at a concentration of 2% by weight in deionized water is combined with the additive composition (or Booster) to provide samples with varying levels of pH as follows:

| Additive Composition | pH |
| --- | --- |
| 0% | 7.84 |
| 0.5% | 8.41 |
| 1% | 8.79 |
| 1.5% | 8.96 |
| 2% | 9.13 |
| 2.5% | 9.27 |

Figure 10:
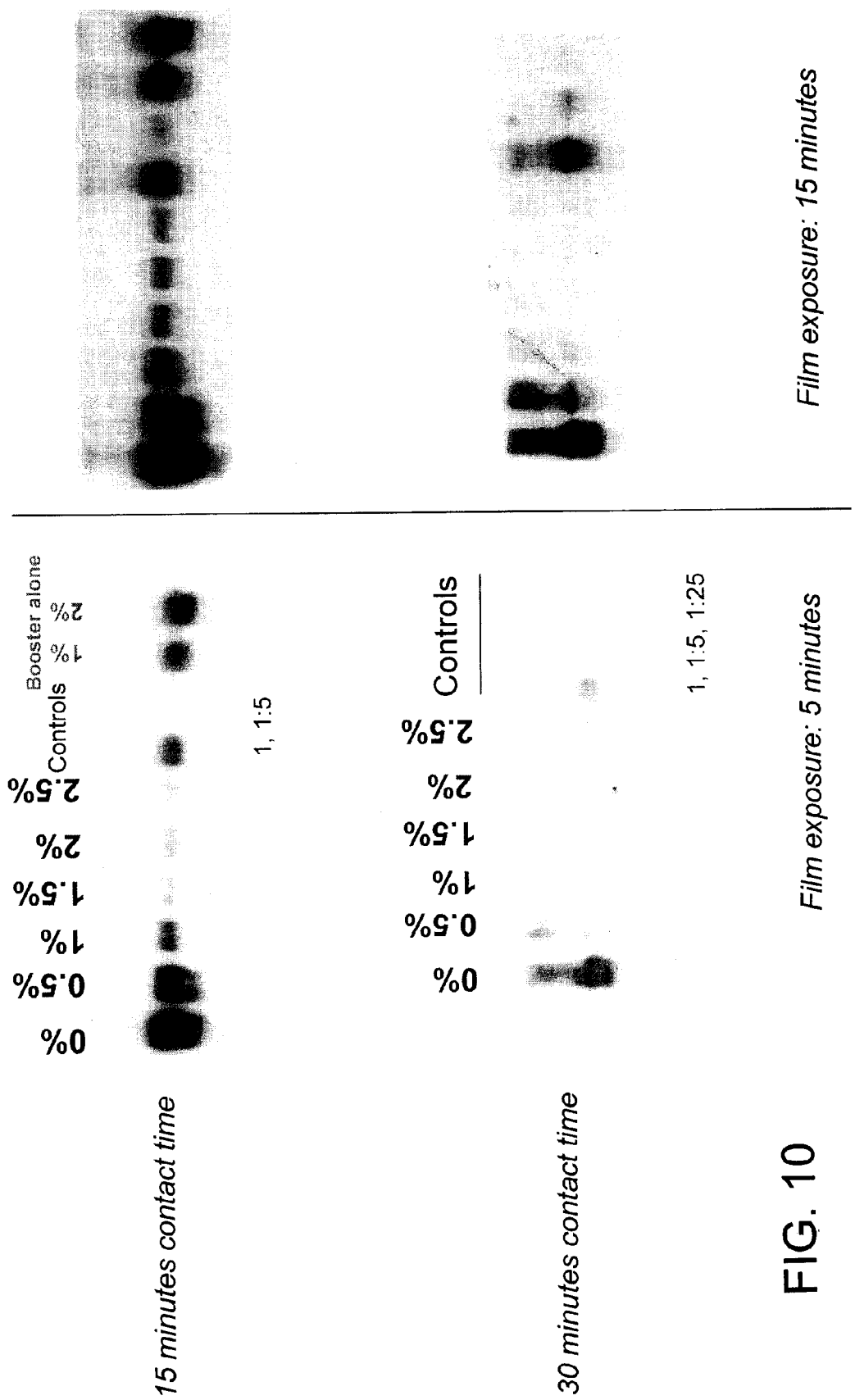
FIG. 10 shows western blot test results for the tests reported in Example 10.

The deionized water has a pH of 7.41. Western blot tests are conducted using these samples and 4% by weight brain homogenate. The results are provided in FIG. 10.

While the invention has been explained in relation to various embodiments, it is to be understood that modifications thereof may become apparent to those skilled in the art upon reading the specification. Therefore, it is to be understood that the scope of the invention specified herein is intended to include all modifications that may fall within the scope of the appended claims.

The invention claimed is:

1. A prion deactivating composition, comprising: at least one prion denaturing agent; and at least one prion deactivating enzyme, wherein the at least one prion denaturing agent comprises at least one copper (II) complexing agent, wherein the composition has a pH in the range from about 7 to about 12 and the at least one prion deactivating enzyme comprises subtilisin 309, and wherein the at least one copper (II) complexing agent comprises tolyltriazole at a concentration in the range from about 1% to about 5% by weight of the composition.

2. The composition of claim 1, further comprising one or more membrane disrupting agents, surfactants, cosolvents, coupling agents, corrosion inhibitors, activity enhancing agents, enzyme stabilizers, oxidizing agents, reducing agents, acids, defoamers, or a mixture of two or more thereof.

3. The composition of claim 1, wherein the copper (II) complexing agent further comprises ethylenediaminetetraacetic acid, 1,1-hydroxyethylidene-1,1 diphosphonic acid, aminotris(methylenephosphonicacid), diethylenetriaminepentamethylenephosphonic acid, ethylenediaminedisuccinic acid, L-glutamic acid N,N-diacetic acid, etidronic acid, one or more additional azoles, one or more salts of one or more of the foregoing, or a mixture of two or more of the foregoing.

4. The composition of claim 1, wherein the copper (II) complexing agent further comprises one or more salts of didecyldimethylammonium with tolyltriazole, benzotriazole, carboxybenzotriazole, ethanol-2,2'-[[methyl-1H-benzotriazol-1-yl)methyl]imino]bis-, or a mixture of two or more thereof.

5. The composition of claim 1, wherein the copper (II) complexing agent further comprises: benzotriazole, carboxybenzotriazole, tetrasodiumethylenediaminedisuccinic acid; trisodiummethylglycinediacetic acid; tetrasodiumtriiminodisuccinic acid; tetrasodium L-glutamic acid N,N-diacetic acid; 6,6'6"-(1,3,5-triazine-2,4,6-triyltriimino)tris(hexanoic acid); ethanol-2,2'-[[methyl-1H-benzotriazol-1-yl)methyl]imino]bis-; didecyldimethylammonium bicarbonate/carbonate; or a mixture of two or more thereof.

6. The composition of claim 1, further comprising a disulfide bond cleaving agent, wherein the disulfide bond cleaving agent comprises one or more of thioglycolate, urea, sodium thiocyanate, glutathione, guanidinium hydrochloric acid, iodoacetic acid, or a mixture of two or more thereof.

7. The composition of claim 1, wherein the weight ratio of the prion denaturing agent to the prion deactivating enzyme is in the range from about 1:50 to about 50:1.

8. The composition of claim 1 further comprising propylene glycol, citric acid, calcium chloride, a linear primary alcohol ethoxylate, an amine oxide, ethanolamine, propylene oxide/ethylene oxide block copolymer, or a mixture of two or more thereof.

9. The composition of claim 1 wherein the copper (II) complexing agent further comprises 6,6'6"-(1,3,5-triazine-2,4,6-triyltriimino)tris(hexanoic acid), didecyldimethylammonium bicarbonate/carbonate, or a mixture of two or more thereof.

10. A method of cleaning a material that is contaminated with infectious proteins, the method comprising contacting the material with a prion deactivating composition, the prion deactivating composition comprising at least one prion denaturing agent and at least one prion deactivating enzyme, wherein the at least one prion denaturing agent comprises at least one copper (II) complexing agent, wherein the composition has a pH in the range from about 7 to about 12 and the at least one prion deactivating enzyme comprises subtilisin 309, and wherein the at least one copper (II) complexing agent comprises tolyltriazole at a concentration in the range from about 1% to about 5% by weight of the composition.

11. The method of claim 10, wherein the prion denaturing agent and the prion deactivating enzyme contact the material simultaneously or sequentially.

12. A method of sterilizing a material that is contaminated with infectious proteins, the method comprising:

(a) contacting the material with a prion deactivating composition, the prion deactivating composition comprising at least one prion denaturing agent and at least one prion deactivating enzyme, wherein the at least one prion denaturing agent comprises at least one copper (II) complexing agent, wherein the composition has a pH in the range from about 7 to about 12 and the at least one prion deactivating enzyme comprises subtilisin 309; and (b) exposing the material to a sterilization medium, wherein the at least one copper (II) complexing agent comprises tolyltriazole at a concentration in the range from about 1% to about 5% by weight of the composition.

13. The method of claim 12 wherein the prion denaturing agent and the prion deactivating enzyme contact the material simultaneously or sequentially.

14. The method of claim 12, wherein the sterilization medium comprises at least one liquid sterilant.

15. The method of claim 14, wherein the liquid sterilant comprises at least one peracetic acid, at least one peroxide, or a mixture of two or more thereof.

16. The method of claim 12, wherein the sterilization medium comprises at least one gaseous sterilant.

17. The method of claim 16, wherein the gaseous sterilant comprises hydrogen peroxide.

18. The method of claim 17 wherein the gaseous sterilant further comprises ammonia.

* * * * *